(12) United States Patent
Yoo et al.

(10) Patent No.: US 10,011,712 B2
(45) Date of Patent: Jul. 3, 2018

(54) HYDROGEL COMPOSITION FOR A MASK BASE AND METHOD FOR MANUFACTURING A HYDROGEL USING SAME

(75) Inventors: Hyun Oh Yoo, Seoul (KR); Jong Chul Kim, Seoul (KR); Jin A. Yang, Suwon-si (KR); Eun Kyoung Choi, Hwaseong-si (KR); Jae Min Lim, Yongin-si (KR)

(73) Assignee: GENIC CO., LTD., Seoul (KR)

( * ) Notice: Subject to any disclaimer, the term of this patent is extended or adjusted under 35 U.S.C. 154(b) by 1123 days.

(21) Appl. No.: 14/349,202

(22) PCT Filed: Sep. 12, 2012

(86) PCT No.: PCT/KR2012/007312
§ 371 (c)(1),
(2), (4) Date: Apr. 2, 2014

(87) PCT Pub. No.: WO2013/051795
PCT Pub. Date: Apr. 11, 2013

(65) Prior Publication Data
US 2014/0239536 A1 Aug. 28, 2014

(30) Foreign Application Priority Data
Oct. 4, 2011 (KR) .................. 10-2011-0100690

(51) Int. Cl.
| | |
|---|---|
| C08L 39/06 | (2006.01) |
| A61K 8/02 | (2006.01) |
| A61K 8/04 | (2006.01) |
| A61K 8/34 | (2006.01) |
| A61K 8/73 | (2006.01) |
| A61K 8/81 | (2006.01) |
| C08J 3/075 | (2006.01) |
| C08J 3/24 | (2006.01) |
| C08J 5/18 | (2006.01) |
| C08L 25/08 | (2006.01) |
| C08L 25/14 | (2006.01) |
| C08L 33/08 | (2006.01) |
| A61Q 19/00 | (2006.01) |

(52) U.S. Cl.
CPC ............ *C08L 39/06* (2013.01); *A61K 8/0212* (2013.01); *A61K 8/042* (2013.01); *A61K 8/342* (2013.01); *A61K 8/345* (2013.01); *A61K 8/73* (2013.01); *A61K 8/733* (2013.01); *A61K 8/737* (2013.01); *A61K 8/8117* (2013.01); *A61K 8/8152* (2013.01); *A61K 8/8182* (2013.01); *A61Q 19/00* (2013.01); *C08J 3/075* (2013.01); *C08J 3/246* (2013.01); *C08J 5/18* (2013.01); *C08L 25/08* (2013.01); *C08L 25/14* (2013.01); *C08L 33/08* (2013.01); *A61K 2800/244* (2013.01); *C08J 2305/00* (2013.01); *C08J 2325/08* (2013.01); *C08J 2325/14* (2013.01); *C08J 2333/02* (2013.01); *C08J 2333/08* (2013.01); *C08J 2339/06* (2013.01); *C08L 2201/54* (2013.01); *C08L 2312/00* (2013.01)

(58) Field of Classification Search
CPC .......... C08L 39/06; C08L 25/08; C08L 25/14; C08L 33/08; A61K 8/0212; A61K 8/042; A61K 8/342; A61K 8/345; A61K 8/73; A61K 8/733; A61K 8/737; A61K 8/8117; A61K 8/8152; A61K 8/8182; A61Q 19/00; C08J 3/075; C08J 3/246; C08J 5/18
USPC ......................................................... 524/459
See application file for complete search history.

(56) References Cited

U.S. PATENT DOCUMENTS

| | | | |
|---|---|---|---|
| 2003/0138479 A1 | 7/2003 | Mizota et al. | |
| 2005/0281869 A1* | 12/2005 | Kruse ................... | A61K 8/345 424/449 |
| 2005/0281881 A1 | 12/2005 | Woeller et al. | |
| 2006/0079640 A1 | 4/2006 | Ishii | |
| 2007/0280974 A1 | 12/2007 | Son et al. | |
| 2008/0226616 A1 | 9/2008 | Schulz et al. | |
| 2011/0076321 A1 | 3/2011 | Woeller et al. | |
| 2011/0182955 A1 | 7/2011 | Roreger et al. | |

FOREIGN PATENT DOCUMENTS

| | | |
|---|---|---|
| CN | 1436071 A | 8/2003 |
| CN | 1738609 A | 2/2006 |
| CN | 1835734 A | 9/2006 |
| CN | 1944495 A | 4/2007 |
| EP | 0909156 A1 | 4/1999 |
| EP | 0850043 B1 | 1/2002 |
| EP | 1293199 A1 | 3/2003 |
| EP | 1904023 A1 | 4/2008 |
| FR | 2832061 A1 | 5/2003 |

(Continued)

OTHER PUBLICATIONS

WO 2009024275 Machine Translation. No Date.*

(Continued)

*Primary Examiner* — Ling Siu Choi
*Assistant Examiner* — Ronald Grinsted
(74) *Attorney, Agent, or Firm* — IP Legal Services, LLC

(57) ABSTRACT

A hydrogel composition includes 0.1 to 10 wt % of a cross-linking agent, 0.2 to 6 wt % of a gelling polymer, 0.5 to 20 wt % of a polyhydric alcohol, and 70 to 90 wt % of purified water to maintain a form without a supporter, be stable without fluidization even when a hydrogel is immersed in cosmetics or pharmaceuticals, and allow the cosmetics or the pharmaceuticals to be uniformly delivered to skin.

8 Claims, 2 Drawing Sheets

(56) References Cited

FOREIGN PATENT DOCUMENTS

| | | | |
|---|---|---|---|
| JP | 54-092618 A | 7/1979 | |
| JP | 10-338619 A | 12/1998 | |
| JP | 11-322535 A | 11/1999 | |
| JP | 2000-514052 A | 10/2000 | |
| JP | 2003-306515 A | 10/2003 | |
| JP | 2004-149463 A | 5/2004 | |
| JP | 2004-231567 A | 8/2004 | |
| JP | 2005-008613 A | 1/2005 | |
| JP | 2006-089459 A | 4/2006 | |
| JP | 2006-513193 A | 4/2006 | |
| JP | 2008-507525 A | 3/2008 | |
| JP | 2010-215553 A | 9/2010 | |
| JP | 2011-102257 A | 5/2011 | |
| KR | 10-2003-0014700 A | 2/2003 | |
| KR | 10-2005-0072459 A | 7/2005 | |
| KR | 10-2009-0101668 A | 9/2009 | |
| KR | 20110008648 A * | 1/2011 | |
| KR | 2011-0008648 A | 9/2012 | |
| WO | 199004383 A1 | 5/1990 | |
| WO | 2004/058211 A1 | 7/2004 | |
| WO | 2006/020166 A1 | 2/2006 | |
| WO | 2009/022761 A1 | 2/2009 | |
| WO | WO 2009024275 A1 * | 2/2009 | ........... A61K 8/0212 |
| WO | 2010/143196 A1 | 12/2010 | |
| WO | WO 2010143196 A1 * | 12/2010 | ............ A61K 8/042 |

OTHER PUBLICATIONS

KR 20110008648A—machine translation.*
Extended European Search Report issued in European Application No. EP12837935.1.
Chinese Office Action issued in Chinese Application No. CN201280048942.6.
Japanese Office Action issued in Japanese Application No. JP2014-534460.
International Search Report and English Translation for PCT/KR2012/007312, dated Jan. 30, 2013, 5 pages.
European Patent Office, Office Action of corresponding EP Patent Application No. 12837935.1, dated May 8, 2017.

* cited by examiner ic fields.

HYDROGEL COMPOSITION FOR A MASK BASE AND METHOD FOR MANUFACTURING A HYDROGEL USING SAME

CROSS-REFERENCE TO RELATED APPLICATIONS

This application is a national stage application of International Patent Application No. PCT/KR2012/007312 filed on Sep. 12, 2012, which claims benefit of priority from Korean Patent Application No. 10-2011-0100690 filed Oct. 4, 2011, which are incorporated by referenced herein in their entirety.

FIELD OF INVENTION

The present invention relates to a hydrogel composition for a mask base, a form of which is maintained without a supporter and has stable properties, even when a hydrogel is immersed in cosmetics or pharmaceuticals, and a method of manufacturing a hydrogel using the same.

BACKGROUND

A hydrogel is a material maintained in a moist state, and fields of application thereof have tended to be diversified into areas such as dressings for wounds, contact lenses, pharmaceuticals, cosmetics delivery media, prostheses, and waste water treating agents. Hydrogel is a material having a three-dimensional hydrophilic polymer network structure including purified water as a dispersion medium, and is highly absorbent, able to absorb large amounts of water, thus having flexibility like that of natural tissue.

Further, the hydrogel may further have novel functions such as controlled release, in which delivery of a material contained therein can be control and susceptibility to expansion and contraction due to stimulation by a pH level, temperature, an electromagnetic field, and light. The hydrogel having the aforementioned characteristics has a structure that is similar to that of a cytosol of a human body, inactive biocompatibility, elasticity like rubber, excellent permeation of oxygen and nutrients, and is thus extensively used in pharmaceutical industrial fields as well as in the cosmetics and biomedical fields.

Recently, a mask pack having an improved humectation, nutrient supplying properties, or dead skin cell removal effects has been developed by using elasticity, close contact properties with skin, and the soft sense of touch of hydrogel.

Non-woven fabrics or cotton are used as a base in mask packs in order to maintain a form thereof, and particularly, non-woven fabrics have a lack of directionality, due to tangled fibers thereof, to thus prevent edges of non-woven fabrics from being fluidized, and accordingly, non-woven fabrics are used extensively as mask pack bases.

However, as described above, since non-woven fabrics are manufactured through a chemical process, skin troubles may occur when a mask pack including non-woven fabrics in the base thereof is applied to the skin of a user; moreover, discarded non-woven fabrics are not easily decomposed in nature, thus causing environmental pollution. Further, there are limitations on the use of cotton in the bases of mask packs, in that manufacturing costs may be increased.

Moreover, mask packs including the non-woven fabrics or cotton as the base is easily dried and has a poor close contact property to skin.

Accordingly, there is demand for the development of a mask pack having no adverse affects on users' skin and excellent wearability. However, while efforts have been made to improve functionality, according to the components contained in mask packs, the base compositions of mask packs have not been developed.

Particularly, hydrogel immersed in cosmetics or pharmaceuticals has not used as the base for the mask pack until now.

SUMMARY

Disclosure

Technical Problem

An aspect of the present invention provides a hydrogel composition for a mask base, a form of which is maintained without a supporter and has stable properties, even when a hydrogel is immersed in cosmetics or pharmaceuticals.

Another aspect of the present invention provides manufacturing of a hydrogel using the hydrogel composition.

Technical Solution

According to an aspect of the present invention, there is provided a hydrogel composition including 0.1 to 10 wt % of a cross-linking agent, 0.2 to 6 wt % of a gelling polymer, 0.5 to 20 wt % of a polyhydric alcohol, and a balance of purified water.

The cross-linking agent may be an acryl-based cross-linking polymer, a styrene-based copolymer, or a mixture thereof.

The acryl-based cross-linking polymer may be a sodium acrylate/C10-30 alkyl acrylate crosspolymer or a potassium acrylate/C10-30 alkyl acrylate crosspolymer, and the styrene-based copolymer may be one or more selected from the group consisting of an acrylate/ethylhexyl acrylate/hema/styrene copolymer, a butylene/ethylene/styrene copolymer, an ammonium acrylate/methylstyrene/styrene copolymer, a styrene/VP copolymer, and a styrene/acrylate copolymer.

The mixture of the acryl-based cross-linking polymer and the styrene-based copolymer may be added in a weight ratio of 2:8 to 8:2.

The gelling polymer may be one or more selected from the group consisting of galactomannan, glucomannan, guar gum, locust bean gum, pluronic, agar, algin, carrageenan, xanthan gum, and gellan.

According to another aspect of the present invention, there is provided a method of manufacturing a hydrogel, which includes adding a cross-linking agent to purified water at room temperature and then performing stirring at a temperature of 40 to 85° C. to manufacture an aqueous solution, dissolving a gelling polymer in a polyhydric alcohol at room temperature, adding the polyhydric alcohol containing the gelling polymer to the aqueous solution, and stirring the resulting solution at 40 to 80° C. to manufacture a hydrogel composition, performing compression coating of the hydrogel composition in a thickness of 0.5 to 2 mm, cooling a hydrogel composition layer that is subjected to the compression coating at room temperature to manufacture the hydrogel, and heat-treating the cooled hydrogel at a temperature of 40 to 85° C. for 12 to 36 hours.

Further, the method may include molding the heat-treated hydrogel into a target form, and immersing the molded hydrogel in cosmetic or pharmaceutical solutions and sealing the hydrogel to manufacture a final product after the heat-treating.

In this case, each surface of the hydrogel may have a film and a non-woven fabric, and specifically, the hydrogel composition layer may have the film on a surface thereof and the non-woven fabric on another surface thereof.

The hydrogel composition may include 0.1 to 10 wt % of the cross-linking agent, 0.2 to 6 wt % of the gelling polymer, 0.5 to 20 wt % of the polyhydric alcohol, and 70 to 90 wt % of purified water.

Strength of the hydrogel manufactured by cooling may be 1.5 to 7.0 kg/cm$^2$.

Advantageous Effects

A hydrogel for a mask base provided according to the present invention has flexibility like natural tissue and thus has excellent wearability on skin. Even in the case that the hydrogel is immersed in cosmetics like essence or pharmaceuticals, since the gel is not fluidized but maintained in form, the hydrogel can be used as a base without a separate base.

Further, even in the case that the cosmetics or the pharmaceuticals are charged in the hydrogel, the resulting hydrogel is stable over a long period of time.

Further, since the hydrogel of the present invention has excellent absorption qualities, a large amount of cosmetics or pharmaceuticals added to non-woven fabrics are uniformly charged in the hydrogel, and thus a large amount of cosmetics or pharmaceuticals are uniformly delivered to skin when the hydrogel adheres thereto.

Further, the hydrogel of the present invention may be variously used in eye patches, hand patches, and atopy patches.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENTS

Best Mode

Figure 1:
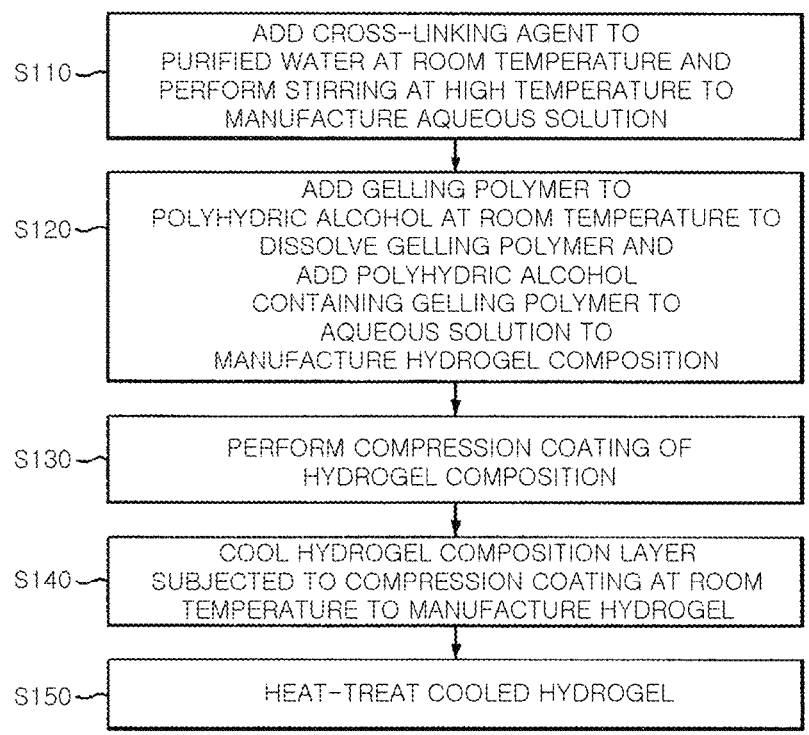
FIG. 1 is a flowchart showing a method of manufacturing a hydrogel according to an embodiment of the present invention.

The present invention relates to a hydrogel composition for a mask base, a form of which is maintained without a supporter and has stable properties, even when a hydrogel is immersed in cosmetics or pharmaceuticals, and a method of manufacturing a hydrogel using the same.

Hereinafter, the present invention will be described in detail.

The hydrogel composition for the mask base includes a cross-linking agent, a gelling polymer, a polyhydric alcohol, and purified water, and a functional additive may be further added according to a use.

Each constituent component will be described below in detail.

The cross-linking agent is an acryl-based cross-linking polymer, a styrene-based copolymer, or a mixture thereof, and the content of the cross-linking agent is 0.1 to 10 wt % and preferably 0.5 to 7 wt %. When the content of the cross-linking agent is less than 0.1 wt %, the gel may be suspended, and when the content is greater than 10 wt %, a residue remains on skin and the gel is fluidized.

The acryl-based cross-linking polymer acts as a bridge, forms a thin film to improve adhesion force and maintain moisture when the hydrogel is used on skin, and provides the soft sense of touch to the hydrogel, and specific examples may include a sodium acrylate/C10-30 alkyl acrylate crosspolymer or a potassium acrylate/C10-30 alkyl acrylate crosspolymer.

Further, the styrene-based copolymer is a film former, physical properties of the gel are increased when cross-linking is performed by heat treatment, and specific examples may include one or two or more selected from the group consisting of an acrylate/ethylhexyl acrylate/hema/styrene copolymer, a butylene/ethylene/styrene copolymer, an ammonium acrylate/methylstyrene/styrene copolymer, a styrene/VP copolymer, and a styrene/acrylate copolymer.

The acryl-based cross-linking polymer and the styrene-based copolymer are added in a weight ratio of 2:8 to 8:2 and preferably 3:7 to 7:3.

In the case where the weight ratio of the acryl-based cross-linking polymer and the styrene-based copolymer is outside the range of 2:8 to 8:2, when the hydrogel is used on skin, viscosity is changed to allow the hydrogel to flow down along skin, and absorption qualities are reduced, and thus it is difficult to charge the cosmetics or the pharmaceuticals in the hydrogel.

The gelling polymer adjusts a form and strength of the gel, and specific examples may include one or two or more selected from the group consisting of galactomannan, glucomannan, guar gum, locust bean gum, pluronic, agar, algin, carrageenan, xanthan gum, and gellan. The content of the gelling polymer is 0.2 to 6 wt % and preferably 0.5 to 5 wt %. When the content of the gelling polymer is less than 0.2 wt %, the form of the gel can be maintained but strength of the gel is high and flexibility is reduced, and thus a close contact property to skin is reduced, and when the content is greater than 6 wt %, it is difficult to maintain the form because the gel droops, it is difficult to manufacture the hydrogel due to reduced elasticity, and adhesion to skin is reduced.

The polyhydric alcohol provides flowability to the hydrogel so that the hydrogel comes into close contact with skin and the cosmetics or the pharmaceuticals permeate skin.

Specific examples of the polyhydric alcohol may include one or two or more selected from the group consisting of 1,2-ethanediol, 1,2-propanediol, 1,3-propanediol, 3-chloro-1,2-propanediol, 2-chloro-1,3-propanediol, and glycerin.

The polyhydric alcohol is used in a content of 0.5 to 20 wt % and preferably 2 to 15 wt %. When the content of the polyhydric alcohol is less than 0.5 wt %, flowability cannot be provided to the hydrogel, and when the content is greater than 20 wt %, the hydrogel may have viscosity.

Further, the functional additive provides stability and functionality to the hydrogel and may be added if necessary, and specific examples may include one or two or more selected from the group consisting of methylparaben, propylparaben, a kojic acid, an α-hydroxy acid, imidazolidinyl urea, Twin 80, and retinol.

The functional additive is used in a content of 0.5 to 3 wt % and preferably 1 to 2 wt %.

The content of purified water is 70 to 90 wt % and preferably 75 to 85 wt %. When the content of purified water is less than 70 wt %, even in the case that a temperature is increased, a gel state may not be changed into a fluidization state, and when the content is greater than 90%, the gel is not formed.

Further, the present invention provides a method of manufacturing the hydrogel using the hydrogel composition, and the method will be described with reference to FIG. 1.

The hydrogel is manufactured by the method including adding the cross-linking agent to purified water at room temperature (23 to 27° C.) and then performing stirring at high temperatures to manufacture the aqueous solution in operation S110, adding the gelling polymer to the polyhydric alcohol at room temperature to dissolve the gelling polymer and then adding the polyhydric alcohol containing the gelling polymer to the aqueous solution to manufacture the hydrogel composition in operation S120, performing compression coating of the hydrogel composition in operation S130, cooling a hydrogel composition layer that is subjected to the compression coating at room temperature to manufacture the hydrogel in operation S140, and heat-treating the cooled hydrogel in operation S150. Further, the method further includes molding the heat-treated hydrogel into a target form in operation S160, and immersing the molded hydrogel in the cosmetic or the pharmaceutical solutions in operation S170 after operation S150. Moreover, the functional additive may be further added to operation S110.

During operation S110, the cross-linking agent is added to purified water and then stirred at a temperature of 40 to 85° C. to manufacture the aqueous solution. Purified water and the cross-linking agent are stirred at the temperature of 40 to 85° C. to be easily thermally cross-linked with a mixture manufactured during the following operation S120.

During operation S120, the gelling polymer is separately dissolved in the polyhydric alcohol, added to the aqueous solution manufactured during operation S110, and stirred at 40 to 80° C. for 0.5 to 2 hours to manufacture the hydrogel composition.

When a stirring temperature of the aqueous solution manufactured during operation S110 and the mixture manufactured during operation S120 is less than 40° C., since the gelling polymer is not dissolved well, physical properties of the hydrogel are reduced, and when the stirring temperature is greater than 80° C., since viscosity of the hydrogel composition is increased, it is difficult to obtain a form and strength is reduced.

Further, when a stirring time is less than 0.5 hours, since the gelling polymer is not uniformly dissolved, strength of the hydrogel is reduced, and when the stirring time is greater than 2 hours, since a gelling ratio of a polymer chain is reduced, strength of the hydrogel is reduced.

During operation S130, compression coating of the hydrogel composition is performed in a thickness of 0.5 to 2 mm by using a roll coater device to form the hydrogel composition layer. When a thickness of the hydrogel composition layer is less than 0.5 mm, since the thickness is small, the hydrogel is torn when the hydrogel adheres to skin, and since the amount of the cosmetics or the pharmaceuticals permeating the gel is small, the cosmetics or the pharmaceuticals are not sufficiently delivered to skin, and when the thickness is greater than 2 mm, since the thickness is large, the hydrogel provides the sense of uncomfortableness and flows down when the hydrogel adheres to skin.

As another example, a film may be compression-coated with the hydrogel composition in a thickness of 0.5 to 2.0 mm by a compression coating device to form the hydrogel composition layer. In this case, the film is not particularly limited as long as the film is easily stripped from the hydrogel and does not affect physical properties of the hydrogel, but a polyethylene terephthalate (PET) film may be used. Further, a non-woven fabric may be provided on another surface of the hydrogel composition layer provided with the film on a surface thereof.

During operation S140, the hydrogel composition layer that is subjected to compression coating is cooled at room temperature for 0.5 to 48 hours to manufacture the hydrogel. When cooling is performed for a period of time of less than 0.5 hours, the hydrogel composition layer having a fluidized phase does not have a form.

During operation S150, a cooled sheet is heat-treated in a drier at 40 to 85° C. for 12 to 36 hours in order to sufficiently charge the cosmetics or the pharmaceuticals in the hydrogel. When a heat treatment time is less than 12 hours, since heat treatment is not ensured, strength is similar to that of a hydrogel in the related art, and hydration or fluidization of the gel occurs when the cosmetics or the pharmaceuticals permeates, and thus the hydrogel cannot be used, and when the heat treatment time is greater than 36 hours, since the hydrogen is excessively dried, a permeation time of the cosmetics or the pharmaceuticals is increased.

The hydrogel manufactured during operation S160 is molded into a target form during operation S160, and the liquid cosmetics or pharmaceuticals are charged in the molded hydrogel during operation S170.

The hydrogel provided according to the present invention has strength of 1.5 to 7 kg/cm$^2$.

Further, the hydrogel of the present invention may be maintained in form without a separate base therein, and is maintained in form without fluidization of the gel even when the hydrogel is immersed in the cosmetics or the pharmaceuticals.

The film may be provided on a surface of the hydrogel manufactured using compression coating of the hydrogel composition in order to prevent damage to the hydrogel during transportation, and the non-woven fabric may be provided on another surface thereof in order to sufficiently absorb the cosmetics or the pharmaceuticals.

When the cosmetics or the pharmaceuticals are charged in the hydrogel, the cosmetics or the pharmaceuticals are infiltrated into the non-woven fabric to permeate the hydrogel, thus being uniformly charged in the surface of the hydrogel.

Further, when the hydrogel provided with the film and the non-woven fabric is used, the non-woven fabric and the film are separated and only the hydrogel is used.

Mode for Invention

Examples will be given hereinafter to help understanding of the present invention, but the following Examples have been described in an illustrative manner, and it is to be understood that various modifications and amendments will be apparent to those skilled in the art without departing from the spirit of the invention, and the modifications and the amendments naturally fall into the scope of the appended claims.

Example 1

2 wt % of the sodium acrylate/C10-30 alkyl acrylate cross polymer as the acryl-based cross-linking polymer and 3 wt % of the styrene/VP copolymer as the styrene-based copolymer were added to 72 wt % of purified water, and then stirred at 60° C. Separately, 2 wt % of carrageenan, 0.5 wt % of xanthan gum, and 0.5 wt % of locust bean gum as the gelling polymer were mixed with 20 wt % of glycerin as the polyhydric alcohol, added to the aqueous solution, and stirred at 70° C. for 2 hours to manufacture the hydrogel composition.

After compression coating of the manufactured hydrogel composition was performed in a thickness of 1.0 mm by using the roll coater device, the hydrogel composition was cooled at room temperature for 1.5 hours. The cooled sheet was heat-treated in the drier (Sejong Scientific, Co., Ltd., DRY OVEN SJ-201DL) at 50° C. for 13 hours to manufacture the hydrogel.

Example 2

The same procedure as Example 1 was performed to manufacture the hydrogel, except that 3 wt % of the potassium acrylate/C10-30 alkyl acrylate crosspolymer as the acryl-based cross-linking polymer, 4 wt % of the styrene/acrylate copolymer as the styrene-based copolymer, 70.2 wt % of purified water, 20 wt % of glycerin, and 1.8 wt % of carrageenan and 1.0 wt % of glucomannan were used as the gelling polymer.

Example 3

The same procedure as Example 1 was performed to manufacture the hydrogel, except that 6 wt % of the butylene/ethylene/styrene copolymer as the styrene-based copolymer was used as the cross-linking agent, and 17 wt % of the polyhydric alcohol, 74.7 wt % of purified water, and 1.0 wt % of carrageenan, 0.8 wt % of xanthan gum, and 0.5 wt % of glucomannan were used as the gelling polymer.

Example 4

The same procedure as Example 1 was performed to manufacture the hydrogel, except that 5 wt % of the sodium acrylate/C10-30 alkyl acrylate cross polymer as the acryl-based cross-linking polymer was used as the cross-linking agent, and 71.4 wt % of purified water, 20 wt % of glycerin, and 2.3 wt % of carrageenan, 0.5 wt % of algin, and 0.8 wt % of locust bean gum were used as the gelling polymer.

Comparative Example 1

The same procedure as Example 1 was performed to manufacture the hydrogel, except that the acryl-based cross-linking polymer and the styrene-based cross-linking polymer are not used, and 20 wt % of glycerin as the polyhydric alcohol, and 2 wt % of carrageenan, 0.5 wt % of xanthan gum, and 0.5 wt % of locust bean gum as the gelling polymer were dispersed in 77 wt % of purified water.

Test Example

The liquid cosmetics were impregnated in the hydrogel manufactured in the Examples and the Comparative Examples to measure physical properties, and the results are described in the following Table 1.

1. Absorbancy of the hydrogel: After the manufacturing initial weight of the manufactured hydrogel was measured, the weight after the hydrogel was deposited in the cosmetics or the pharmaceuticals for one day (weight after deposition) was measured to evaluate absorbancy calculated by the following Equation.

$$\text{Absorbancy}(\%) = \{(\text{weight after deposition} - \text{initial weight})/(\text{initial weight})\} \times 100 \quad \text{[Equation]}$$

2. Stability: The hydrogel was cut to have a size of 2 cm×2 cm and then immersed in the phosphate buffer solution (pH 7.4, 80 ml), and the physical change of the gel (fluidization of the gel) was measured in the shaking incubator rotating at 200 rpm under the condition of 37° C. by the naked eye after 60 minutes, 5 hours, 10 hours, and 24 hours, and evaluated based on the following evaluation standard.

◎: Maintenance of properties

O: The gel is fluidized in an area of less than 10% of the total area

□: The gel is fluidized in an area of less than 30% of the total area

Δ: The gel is fluidized in an area of less than 50% of the total area

X: The gel is fluidized in an area of less than 70% of the total area

3. Strength: Compressive strength of the gel was measured by using the SUN Rheo Meter Compac-100 II (Sun Scientific Co., Ltd., Japan). The sample for measuring compressive strength was cylindrical and had the width of 50 mm and the length of 50 mm.

When compressive strength was measured, the adapter had the diameter of 10 mm, the entrance (admission) distance was 0.15 mm, and maximum stress of the load cell was 10 kg (maximum 20 kg).

TABLE 1

| Classification | | Example 1 | Example 2 | Example 3 | Example 4 | Comparative Example 1 |
|---|---|---|---|---|---|---|
| Hydrogel absorbancy | | 240 | 220 | 190 | 170 | 120 |
| Stability | 60 minutes | ◎ | ◎ | ◎ | ◎ | ◎ |
| | 5 hours | ◎ | ◎ | ◎ | O | Δ |
| | 10 hours | O | O | O | Δ | X |
| | 24 hours | O | Δ | Δ | X | — |
| Strength (kg/cm$^2$) | | 6.4 | 5.3 | 5.4 | 5.1 | 1.0 |

As shown in Table 1, it was confirmed that Examples 1 to 4 of the present invention had excellent absorbancy, stability (fluidization of the gel), and strength. On the other hand, absorbancy, stability, and strength of Comparative Example 1 were not excellent as compared to Examples 1 to 4.

Figure 2:
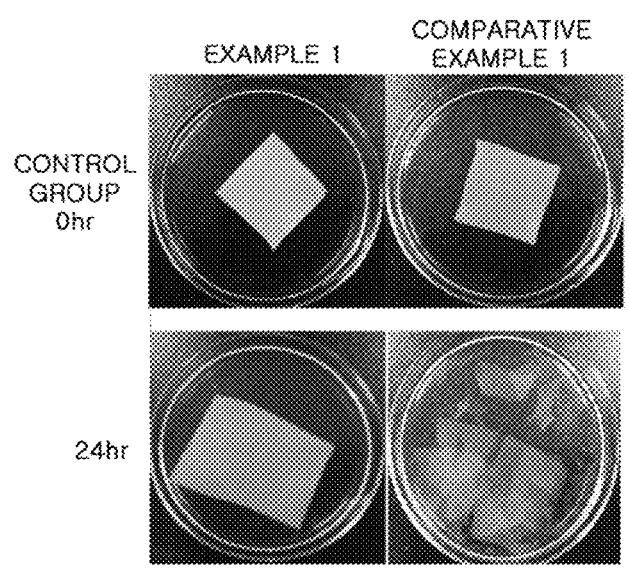
FIG. 2 shows stability of hydrogels manufactured according to Example 1 and Comparative Example 1.

FIG. 2 shows stability of the hydrogel manufactured according to Example 1 and Comparative Example 1, and it could be confirmed that the gel was not fluidized but stable properties were maintained even after 24 hours in Example 1 but the gel was fluidized after 24 hours in Comparative Example 1.

What is claimed is:

1. A hydrogel composition for a mask base comprising:
   0.1 to 10 wt % of a cross-linking agent based on a total weight of the hydrogel composition, wherein the cross-linking agent is a mixture of an acryl-based cross-linking polymer and a styrene-based copolymer, and wherein the mixture of the acryl-based cross-linking polymer and the styrene-based copolymer is added in a weight ratio of 2:8 to 8:2;
   0.2 to 6 wt % of a gelling polymer, based on a total weight of the hydrogel composition;
   0.5 to 20 wt % of a polyhydric alcohol, based on a total weight of the hydrogel composition; and
   70 to 90 wt % of purified water, based on a total weight of the hydrogel composition.

2. The hydrogel composition of claim 1, wherein the acryl-based cross-linking polymer is a sodium acrylate/C10-30 alkyl acrylate crosspolymer or a potassium acrylate/C10-30 alkyl acrylate crosspolymer.

3. The hydrogel composition of claim 1, wherein the styrene-based copolymer is one or more selected from the group consisting of an acrylate/ethylhexyl acrylate/hema/styrene copolymer, a butylene/ethylene/styrene copolymer, an ammonium acrylate/methylstyrene/styrene copolymer, an N-vinylpyrrolidone/styrene, and a styrene/acrylate copolymer.

4. The hydrogel composition of claim 1, wherein the gelling polymer is one or more selected from the group consisting of galactomannan, glucomannan, guar gum, locust bean gum, poloxamers, agar, algin, carrageenan, xanthan gum, and gellan.

5. The hydrogel composition of claim 1, wherein the polyhydric alcohol is one or more selected from the group consisting of 1,2-ethanediol, 1,2-propanediol, 1,3-propanediol, 3-chloro-1,2-propanediol, 2-chloro-1,3-propanediol, and glycerin.

6. A method of manufacturing a hydrogel composition for a mask base of claim 1, the method comprising:
   adding a cross-linking agentto purified water at room temperature and then performing stirring at a temperature of 40 to 85° C. to manufacture an aqueous solution;
   dissolving a gelling polymer in a polyhydric alcohol at room temperature, adding the polyhydric alcohol containing the gelling polymer to the aqueous solution, and stirring the resulting solution at 40 to 80° C. to manufacture a hydrogel composition;
   performing compression coating of the hydrogel composition in a thickness of 0.5 to 2 mm;
   cooling a hydrogel composition layer that is subjected to the compression coating at room temperature to manufacture the hydrogel; and
   heat-treating the cooled hydrogel at a temperature of 40 to 85° C. for 12 to 36 hours.

7. The method of claim 6, further comprising:
   molding the heat-treated hydrogel into a target form; and
   immersing the molded hydrogel in cosmetic or pharmaceutical solutions.

8. The method of claim 6, wherein strength of the cooled hydrogel is 1.5 to 7.0 kg/cm$^2$.

* * * * *